(12) United States Patent
Coote et al.

(10) Patent No.: US 7,943,128 B2
(45) Date of Patent: May 17, 2011

(54) ANTI-MICROBIAL COMPOSITIONS COMPRISING A CATIONIC PEPTIDE AND A GLYCYLGLYCINE ENDOPEPTIDASE

(75) Inventors: Peter John Coote, Fife (GB); Shirley Graham, Dundee (GB)

(73) Assignee: The University Court of the University of St Andrews, Fife (GB)

( * ) Notice: Subject to any disclaimer, the term of this patent is extended or adjusted under 35 U.S.C. 154(b) by 290 days.

(21) Appl. No.: 12/225,441

(22) PCT Filed: Mar. 29, 2007

(86) PCT No.: PCT/GB2007/001157
§ 371 (c)(1),
(2), (4) Date: Sep. 22, 2008

(87) PCT Pub. No.: WO2007/113499
PCT Pub. Date: Oct. 11, 2007

(65) Prior Publication Data
US 2009/0130185 A1    May 21, 2009

(30) Foreign Application Priority Data

Mar. 31, 2006  (GB) .................................. 0606493.5
Aug. 4, 2006   (GB) .................................. 0615500.6

(51) Int. Cl.
*A61K 38/10*   (2006.01)
*A61K 38/17*   (2006.01)
*A61K 38/48*   (2006.01)
*A61L 2/16*    (2006.01)

(52) U.S. Cl. ....... 424/94.67; 422/32; 424/404; 424/445; 514/2.4; 514/2.9; 514/3.2

(58) Field of Classification Search ........................ None
See application file for complete search history.

(56) References Cited

U.S. PATENT DOCUMENTS

| 4,810,777 A | 3/1989 | Zasloff ......................... 530/326 |
| 4,980,163 A | 12/1990 | Blackburn et al. ......... 434/94.63 |
| 2003/0211995 A1* | 11/2003 | Kokai-Kun et al. ............ 514/12 |

FOREIGN PATENT DOCUMENTS

WO    WO 99/04809    2/1999

(Continued)

OTHER PUBLICATIONS

Clark, et al., "A Novel Antimicrobial Peptide from Bullfrog (*Rana catesbeiana*) Skin, Structurally Related to the Bacterial Antibiotic, Polymyxin", *The Journal of Biological Chemistry*, vol. 269, No. 14, pp. 10849-10855 (1994).

(Continued)

*Primary Examiner* — Jeffrey E Russel
(74) *Attorney, Agent, or Firm* — Drinker Biddle & Reath LLP (57) ABSTRACT

There is provided an anti-microbial composition comprising a cationic peptide and a glycineglycine endopeptidase. The composition has been found to be synergistic against bacteria, especially Gram positive bacteria such as *Staphylococcus aureus* MSSA or MRSA. In one embodiment the composition comprises ranalexin, dermaseptin, magainin or mixtures thereof together with lysostaphin. The composition is useful for treating surfaces, including a wound surface in a patient or surfaces of an object (e.g. surgical instrument) or room.

30 Claims, 12 Drawing Sheets

FOREIGN PATENT DOCUMENTS

WO    WO 2004/052308    6/2004

OTHER PUBLICATIONS

Giacometti, et al., "In-vitro Activity of Cationic Peptides Alone and in Combination with Clinically Used Antimicrobial Agents Against *Pseudomonas aeruginosa*", *Journal of Antimicrobial Chemotherapy* (1999) 44, 641-645.

Lu, et al., "Peptidoglycan Recognition Proteins Are a New Class of Human Bactericidal Proteins", *The Journal of Biological Chemistry*, vol. 281, No. 9, pp. 5895-5907, Mar. 1, 2006.

Polak, et al., "In vitro Activity of Recombinant Lysostaphine-Antibiotic Combinations Toward Methicillin-Resistant *Staphylococcus aureus*", *Diagn Microbiol Infect Dis*, 1993: 17: 265-270.

* cited by examiner

SEQUENCE LISTING

<160> NUMBER OF SEQ ID NOS: 1

<210> SEQ ID NO 1
<211> LENGTH: 20
<212> TYPE: PRT
<213> ORGANISM: Rana catesbeiana

<400> SEQUENCE: 1

```
Phe Leu Gly Gly Leu Ile Lys Ile Val Pro Ala Met Ile Cys Ala Val
1               5                   10                  15

Thr Lys Lys Cys
            20
```

ANTI-MICROBIAL COMPOSITIONS COMPRISING A CATIONIC PEPTIDE AND A GLYCYLGLYCINE ENDOPEPTIDASE

The present invention relates to compositions to inhibit propagation of prokaryotic organisms, such as bacteria.

Various types of agents with bactericidal or bacteriostatic activity are known, for example antibiotics. However, increasingly, microbial resistance to antibiotics is creating difficulty in treating some infections. Particular difficulties arise with infections caused by *Staphylococcus aureus* which is an important cause of hospital and community infections. In hospitals, patients who have been catheterised or who are recovering from surgical procedures have a significantly higher rate of infection with considerable morbidity and mortality. In some countries the problem is exacerbated because the majority of nosocomial *S. aureus* infections are caused by strains that are multiply resistant to antibiotics. These multiply drug-resistant strains are termed "MRSA" (methicillin-resistant *Staphylococcus aureus*). There has been a dramatic increase in the proportion of *S. aureus* isolates classified as MRSA. For example, in the UK in 2004, 40% of all *S. aureus* bacteraemia isolates were classified as MRSA. It is therefore clear that MRSA is a considerable problem, especially in the developed world.

Specific combinations of antimicrobials have been developed to treat microorganism-derived diseases in humans and animals, especially diseases caused by bacteria resistant to antibiotics. For example, infection with the Gram positive bacterium *Mycobacterium tuberculosis* (the etiologic agent of tuberculosis), which easily acquires antibiotic resistance, may be more effectively treated with a combination of different antibiotics. Furthermore, combination of the beta-lactam antibiotic amoxicillin and the beta-lactamase inhibitor clavulanic acid (Nadler J P et al., Chest, 1991, Vol. 99, pp. 1025-1026) has resulted in the development of an effective treatment for some penicillin-resistant bacteria. Thus, combination approaches to treating bacterial infection have the benefit of being less likely to induce resistance in bacteria due to targeting multiple, different sites of action. If combinations of antimicrobials display a synergistic mode of action they also have the added benefit of being cheaper as the combination uses lower quantities of the antimicrobials than if they were used alone. Nosocomial infections often involve multi-drug resistant bacteria and these result in increased mortality, morbidity and cost of treating affected patients.

Antimicrobial agents are derived from a wide variety of sources. For example, the protein ranalexin is secreted by the North American bullfrog (*Rana catesbeiana*) and consists of 20 amino acids (N-terminus F-L-G-G-L-I-K-I-V-P-A-M-I-C-A-V-T-K-K-C C-terminus) (SEQ ID NO 1) with a single intramolecular disulphide bond forming a heptapeptide ring within the molecule (Clark et al., J Biol Chem, 1994, Vol. 269 No. 14, pp 10849-10855). Ranalexin has a similar structure to the bacterial antibiotic polymyxin, which is also an amphipathic peptide with a heptapeptide ring. Ranalexin has been successfully tested in vivo for preventing vascular graft infection caused by antibiotic resistant Gram positive *Staphylococcus epidermidis* (Giacometti et al., J Antimicrob Chemother, 2000, Vol. 46, pp 751-756). Other cationic amphipathic peptides have also been shown to have antimicrobial activity. To date, more than 500 such peptides have been described (see Zasloff Nature, 2002, 415:389-395). These peptides are all amphipathic molecules: they have hydrophobic domains comprising non-polar amino acid side chains, and hydrophilic domains of polar and positively charged residues. For example dermaseptins, such as dermaseptin S3, exhibit antimicrobial activity, e.g. against yeasts, even in a truncated form (Coote et al., Antimicrob Agents Chemother, 1998, Vol. 42, No. 9, pp 2160-2170).

Functional studies of cationic peptides such as ranalexin or magainin2 in combination with clinically used antibiotics such as Clarithromycin or Polymyxin E have been successfully conducted in vitro against clinical isolates of the Gram negative bacteria *Pseudomonas aeruginosa*. A combination of the peptides with these antibiotics resulted in a synergistic effect (Giacometti et al., J Antimicrob Chemother, 1999, Vol. 44, pp 641-645.) Magainins are derived from the African clawed frog *Xaenopus laevis* and dermaseptins from the South American arboreal frog *Phyllomedusa sauvagli* (comprising s1 to s5) are 23-34 amino acids in length, cationic and amphipathic, and they are capable of adopting an alpha-helical conformation.

Certain enzymes can also exhibit an antimicrobial activity, for example by interfering with the bacterial cell wall. One example of such an enzyme is lysozyme, which is isolatable from tear liquid or egg white. Lysozyme hydrolyses the beta-1,4 glycosidic bond between N-acetyl glucosamine and N-acetylmuramic acid, thus leading to rupture of the wall. Another enzyme which also targets the bacterial cell wall is lysostaphin. This 27 kDa zinc-dependent metallopeptidase, which is secreted by strains of *Staphylococcus simulans* and *S. staphylolyticus*, cleaves the glycine-glycine bonds in the pentaglycine cross bridges between the peptidoglycan-layers of staphylococcal cell walls, leading to cell lysis. Lysostaphin is capable of killing *Staphylococcus aureus* at low concentrations within minutes (Wu et al, Antimicrob Agents Chemother, 2003, Vol. 47, No. 11, pp 3407-3414). Unfortunately, a high level of resistance to lysostaphin occurs after exposure to sub-inhibitory levels. In one approach for overcoming problems of resistance, lysostaphin was used with a beta-lactam antibiotic, which suppressed the resistance of the bacteria to lysostaphin and further resulted in a synergistic killing effect (Kiri et al., Antimicrob Agents Chemother, 2002, Vol. 46, no. 6, pp 2017-2020).

The present invention is founded on the realization that lysostaphin and ranalexin act synergistically in their antibacterial action.

Resistance to lysostaphin can be easily selected in vitro and has been cited as a potential problem if the enzyme is developed for commercial application (Climo et al., 2001, Antimic Agents Chemother, 45:1431-1437). Lysostaphin is also immunogenic, so that patients previously exposed to the enzyme could potentially produce antibodies that sequester the compound and thus reduce activity (Walsh et al., 2003, Antimic Agents Chemother, 47:554-558). Our demonstration of inhibitory synergy between combinations of ranalexin and lysostaphin could address both of these potential problems. Firstly, resistance is less likely to occur when bacteria are exposed to a combination of two compounds with differing modes of action, and secondly, the synergistic nature of the combination means that reduced amounts of each individual compound are required to induce the same killing effect allowing the use of lower levels of lysostaphin in circulation which are less likely to induce an immunogenic response whilst maintaining the efficacy of the treatment.

However, there remains a need for additional antimicrobial agents and therapies, especially those aimed at targeting multiply resistant bacteria such as MRSA.

According to the present invention there is provided a composition comprising a cationic peptide and a glycylglycine endopeptidase.

The composition comprising a cationic peptide and a glycylglycine endopeptidase inhibits propagation of a prokaryote, such as a Gram positive bacterium, for example *Staphylococcus* sp. The bacterium may be *Staphylococcus aureus*, for example *Staphylococcus aureus* MSSA or MRSA. In one embodiment the composition is bactericidal, ie, the bacteria are killed by the composition.

It is believed that the positively charged residues of the cationic peptide interacts with the bacterial cell membrane, especially with the negatively charged phospholipids, disturbing membrane integrity and stability. Eukaryotic cell membranes only possess a very low content of negatively charged phospholipids, which results in the high specificity and selectivity of the abovementioned proteins for bacterial membranes.

The term "inhibits propagation" refers to a bacteriostatic action (ie, the prevention of bacterial colonization on a disinfected surface treated with the composition of the present invention relative to an untreated surface) and also refers to a bactericidal action (ie, active killing of the bacteria).

The combination of the two components present in the composition results in a synergistic antibacterial effect. Our results have shown that a bactericidal effect can be produced, and requires smaller quantities of the two components than either component when used alone. This synergistic effect has the advantage of reducing costs.

Additionally, since each of the two components acts upon the bacteria in a different way, it is therefore expected that the combination would prevent the acquisition of resistance by bacteria to the composition. This feature of the composition is of particular importance for bacteria such as MRSA strains of *Staphylococcus aureus* which are usually adept at acquiring resistance against new therapies.

In one embodiment the cationic peptide of the composition is ranalexin, dermaseptin, magainin or a mixture thereof. The reference to dermaseptin includes truncated derivatives thereof.

In one embodiment the glycylglycine endopeptidase of the composition is lysostaphin.

The composition of the present invention can be in the form of an aqueous solution or suspension. In this embodiment the composition can be applied to the surface to be treated by spraying, for example as an aerosol spray.

The composition of the invention can be applied to a solid porous matrix. The composition remains effective even when dried on the matrix. The matrix could be a bandage, wipe, swab, medical thread, surgical garment, wound dressing or the like.

In one embodiment, the composition comprises the cationic peptide at a concentration of 0.001 µg/ml or above, for example 0.1 µg/ml to 100 µg/ml preferably 4 µg/ml to 100 µg/ml. Suitable concentrations include 1 µg/ml or above, more preferably 5 µg/ml to 100 µg/ml. For some applications a concentration of 10 µg/ml or above (for example 10 µg/ml to 100 µg/ml) can be used.

In one embodiment, the composition comprises the glycylglycine endopeptidase at a concentration of 0.01 µg/ml or above, for example 0.1 µg/ml to 100 µg/ml. Such concentrations include 0.05 µg/ml or above, for example 0.15 µg/ml or above, preferably 0.45 µg/ml or above. For some applications a concentration of 0.6 µg/ml or above may be suitable, for example 0.6 µg/ml to 100 µg/ml.

In a preferred embodiment the composition comprises ranalexin and lysostaphin. An effective concentration of ranalexin and lysostaphin preferably comprises a concentration of 5 µg to 50 µg ranalexin per ml and 0.15 µg to 1.05 µg lysostaphin per ml.

The present invention also provides a wound dressing containing the composition, and a medical device or surgical instrument containing or coated with the composition. The wound dressing, which may for example be a plaster, bandage or the like, can optionally be impregnated with the composition or include one or more layers impregnated with the composition. The surgical instrument or medical device may be coated with the composition, for example by spraying or dipping to reduce the risk of spreading infection from or to a patient. Exemplary surgical instruments include, but are not limited to, a scalpel, catheter, drainage tube, clamp, needle, clip, swab, medical thread and the like. The medical device includes any device attached permanently or temporarily to the body of a patient. Exemplary medical devices include, but are not limited to, endoprotheses, grafts (including vascular grafts), stents, sutures, replacement joints, pins and plates for fixing bones, stoma devices (including a PEG-device), contraceptive implants, and the like.

The present invention also provides a method of inhibiting propagation of bacteria, such as *Staphylococcus aureus*, by applying the composition according to the invention to a surface where bacterial propagation is undesirable.

In one embodiment, the surface is a surface of an object (surgical instrument, medical device, furniture, frequently handled items etc) or of a room (wall, floor, ceiling etc) and the composition is used to disinfect the surface of any existing bacterial population thereon and/or to inhibit re-colonization of the surface by bacteria. The bacteria can be *Staphylococcus aureus*.

The composition can be applied as a wash or conveniently can be applied as a spray. Optionally a wipe impregnated with the composition can be used.

In an alternative embodiment, the surface is a body surface of a patient. In one embodiment the surface is a wound caused by accident, trauma or surgery.

The composition can be applied to the body surface directly (for example as a spray, lotion or wash) or as a wound dressing containing the composition. Application of the composition can be especially useful prior to or following surgery as a prophylactic treatment to prevent or reduce bacterial infection. Of course the composition can also be used to effectively treat an existing or established bacterial infection. As indicated above, the composition of the present invention is specifically efficacious against *Staphylococcus aureus*, including MSSA and MRSA.

In one embodiment the bacteria will be killed by application of the composition.

The present invention also provides the composition as described above for use in treating a surface of an object or a surface of a room to combat bacterial propagation thereon. The bacteria can be *Staphylococcus* sp., for example *Staphylococcus aureus*.

The present invention also provides the composition as described above for use in combating a bacterial infection in a patient. The bacteria can be *Staphylococcus aureus*.

Another aspect of the present invention provides a method for inhibiting propagation of a prokaryotic organism by using a composition comprising a cationic peptide and a glycylglycine endopeptidase, wherein the prokaryotic organism has a cell wall comprising a phospholipid-membrane comprising one or more acidic phospholipids and a mureinsacculus comprising at least two murein-layers cross-linked via a peptide bridge comprising at least one peptide bond connecting at least two glycine-residues, wherein said composition disintegrates said cell wall, and wherein said glycylglycine endopeptidase hydrolyses said peptide bond connecting the at least two glycine-residues and wherein said cationic peptide interacts with said membrane. In one embodiment the prokaryotic organism is killed by the composition.

The present invention will now be described in more detail by reference to the following examples and figures in which.

EXAMPLE 1

Figure 1:
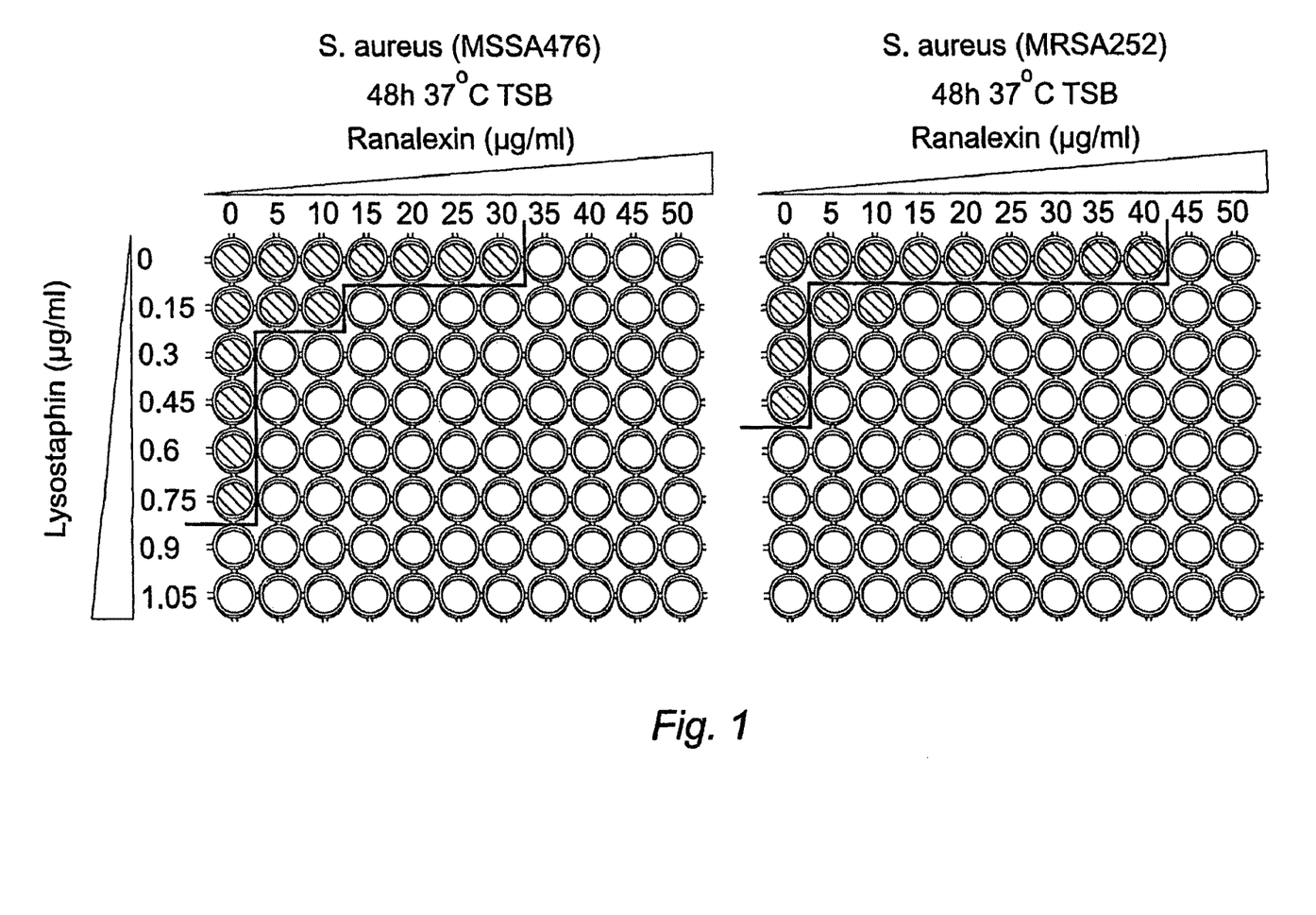
FIGS. 1 and 2 show growth inhibition of *Staphylococcus aureus* strains MSSA476 (left) and MRSA252 (right) at different concentrations of ranalexin and lysostaphin in a microtitre plate assay.

*Staphylococcus aureus* strains MSSA476 (left) and MRSA252 (right) were cultivated in TSB (Tryptone Soya Broth; Oxoid Basingstoke, UK) to mid-exponential phase. Cultures were then diluted in fresh medium to a starting optical density of 600 nm of 0.001 (approximately $1.0 \times 10^6$ cells/ml). Growth of 100 µl volume cultures was measured in 96-well culture plates using TSB as control for 37° C. for 48 hours without shaking in the presence of 0 µg ranalexin/ml medium to 50 µg/ml, increasing stepwise by 5 µg/ml. 8 samples were cultivated for each concentration of ranalexin and to each such sample a different concentration of lysostaphin was added from 0 µg/ml to 1.05 µg/ml in steps of 0.15 µg/ml. The antibacterial activity was measured by reduced turbidity measured by optical density by scanning on an Image Scanner (GE Healthcare UK Ltd) using Image Master Labscan v.3 software. The results are shown in FIG. 1. The concentration of ranalexin is indicated above the respective column, each well of a column having the same ranalexin concentration. The wells of each row contain lysostaphin at a final concentration of 0 µg lysostaphin per ml medium to 1.05 µg/ml (as indicated on left), increasing stepwise by 0.15 µg/ml. For *S. aureus* MSSA476 cultivated in the absence of lysostaphin, ranalexin provides an inhibitory effect at concentrations above 30 µg/ml medium (typically 35 to 40 µg/ml). In the absence of ranalexin, a lysostaphin concentration above 0.75 µg/ml is effective (MSSA476 had an MIC of approximately 0.75 µg/ml and MRSA252 approximately 0.45 µgml). The combination of ranalexin and lysostaphin reduces the necessary amount of each of the compounds by providing a synergistic antimicrobial effect.

For example, in the presence of ranalexin at a minimum concentration of 5 µg/ml or higher, a concentration of 0.15 µg/ml lysostaphin completely inhibited the growth of MRSA252 over 48 hours, and 5 µg/ml ranalexin with 0.3 µg/ml lysqstaphin inhibited MRSA475 over the same period. In the presence of lysostaphin at a minimal concentration of 0.15 µg/ml or higher, the presence of ranalexin at more than 10 µg/ml medium is sufficient for achieving such effect.

*S. aureus* MRSA252 cultivated in the absence of lysostaphin is inhibited by ranalexin at concentrations above 40 µg/ml medium; in the absence of ranalexin, a lysostaphin concentration above 0.45 µg/ml is needed for such effect. Combination of ranalexin and lysostaphin again reduces the necessary amount of each of the compounds. The inhibitory effect can be observed at concentrations higher than 0 µg/ml for both lysostaphin and ranalexin.

EXAMPLE 2

*Staphylococcus aureus* strains MSSA476 (left) and MRSA252 (right) were cultivated in TSB medium as described in Example 1, except for the narrower concentration ranges of ranalexin and lysostaphin. Ranalexin is provided at concentrations of 0 µg/ml, 0.5 µg/ml and 1 µg/ml to 10 µg/ml, increasing stepwise by 1 µg/ml medium, and lysostaphin concentrations of 0 µg/ml to 0.2 µg/ml, with intermediate concentrations of 0.01 µg/ml, 0.025 µg/ml, 0.05 µg/ml, 0.075 µg/ml, 0.1 µg/ml and 0.15 µg/ml as indicated in FIG. 2.

Figure 2:
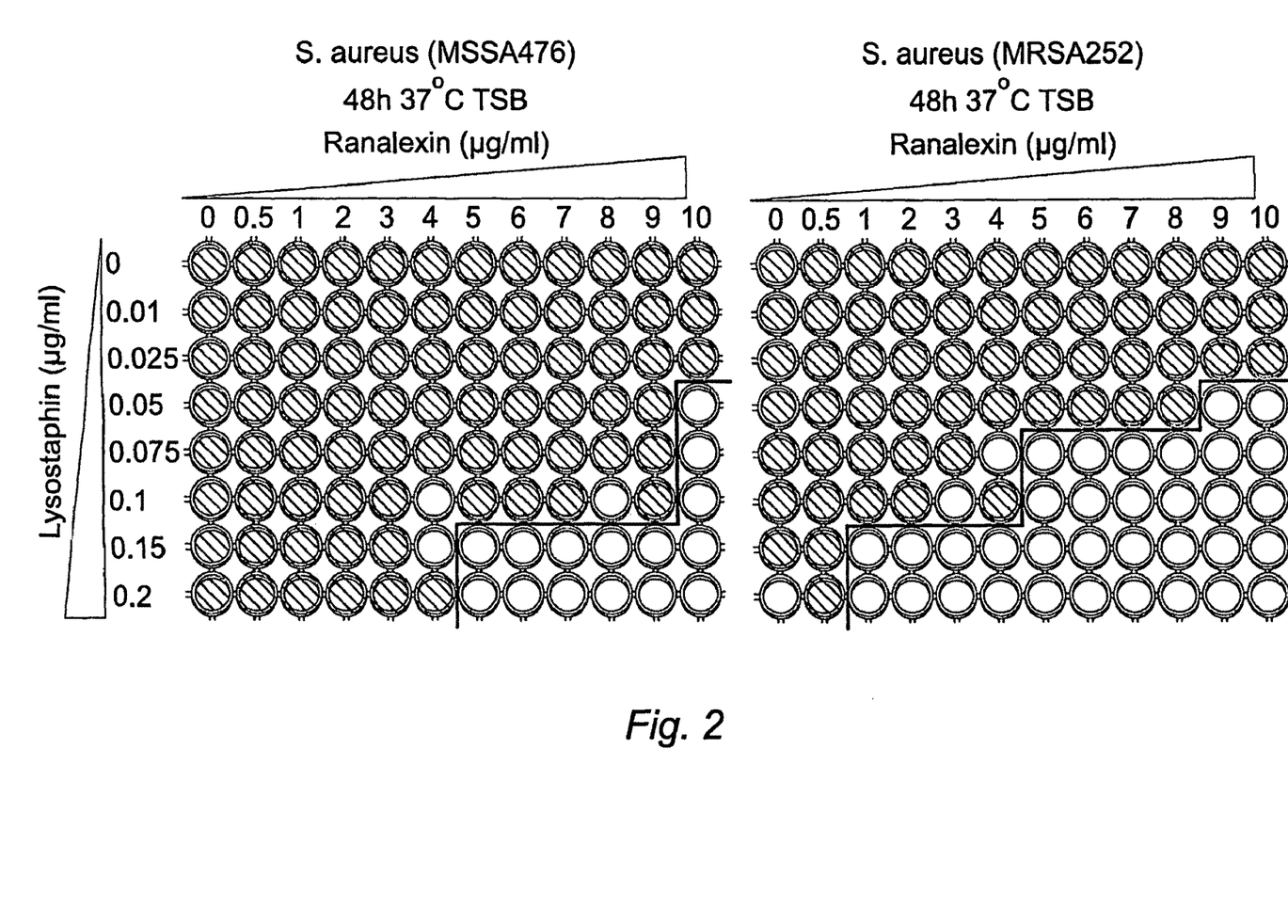

By studying lower concentrations of the two compounds, we were able to more accurately define the boundaries of growth (FIG. 2). Thus, exposure of MRSA252 to 1 µg ml$^{-1}$ ranalexin with 0.15 µg ml$^{-1}$ lysostaphin represented the minimum effective levels of the compounds that abolished growth. Similarly, exposure of MSSA476 to 5 µg ml$^{-1}$ ranalexin with 0.15 µg ml$^{-1}$ lysostaphin represented the minimum effective levels that abolished growth of this strain.

EXAMPLE 3

Figure 4:
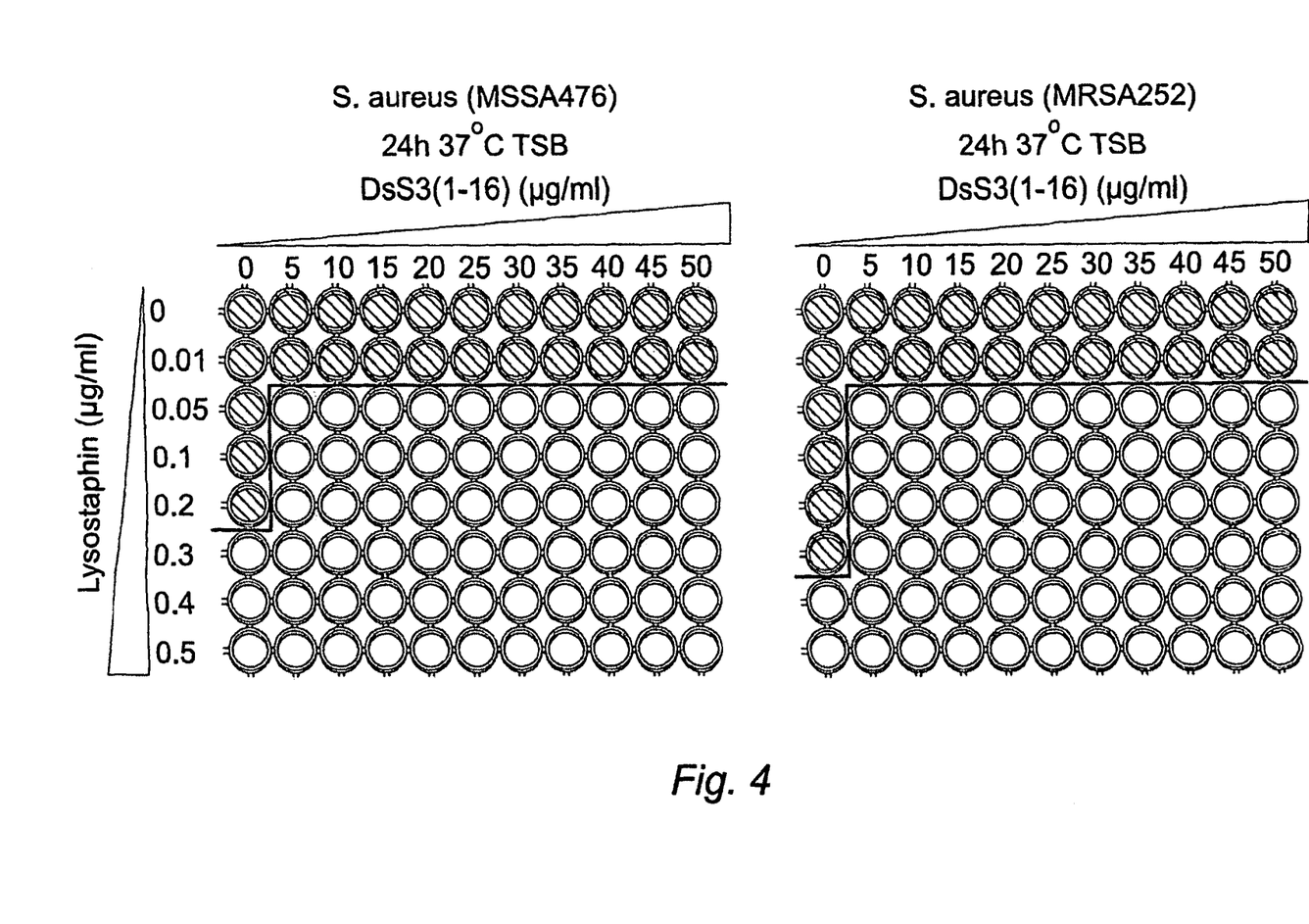
FIG. 4 shows growth inhibition of *Staphylococcus aureus* strains MSSA476 (left) and MRSA252 (right) at different concentrations of a C-terminally truncated form of dermaseptin S3 (amino acids 1-16) labelled as "DsS3(1-16)", and lysostaphin in a microtitre plate assay.

Staphylococcus aureus strains MSSA476 (left) and MRSA252 (right) were cultivated in TSB medium as described in Example 1, except for ranalexin being replaced by dermaseptin s3(1-16) (a truncated derivative of dermaseptin s3, Mor & Nicolas, Eur J Biochem, 1994, 219:31635-31641) at the same concentrations (0 µg/ml to 50 µg/ml) as indicated in FIG. 4.

Dermaseptin s3(1-16) alone had little inhibitory effect on either strain of *S. aureus* (up to 50 µg ml$^{-1}$), but when applied in combination with lysostaphin, significant synergistic inhibition was observed (FIG. 4). For example, the minimum concentrations of the combined compounds that completely inhibited visible growth were 5 µg ml$^{-1}$ dermaseptin s3(1-16) and 0.05 µg ml$^{-1}$ lysostaphin.

EXAMPLE 4

Figure 3:
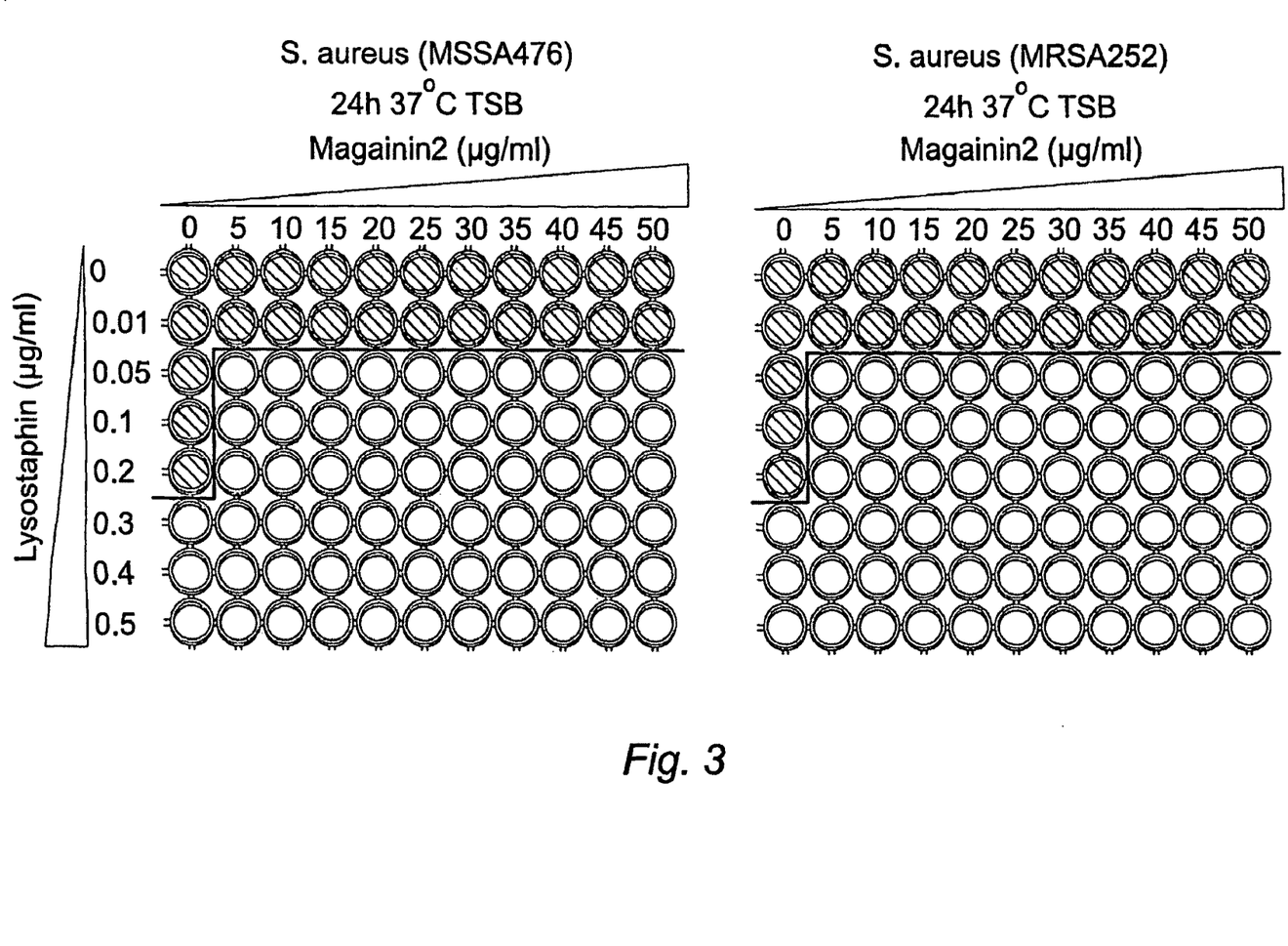
FIG. 3 shows growth inhibition of *Staphylococcus aureus* strains MSSA476 (left) and MRSA252 (right) at different concentrations of magainin2 and lysostaphin in a microtitre plate assay.

*Staphylococcus aureus* strains MSSA476 (left) and MRSA252 (right) were cultivated in TSB medium as described in example 1, except for Ranalexin being replaced by with Magainin2 at the same concentrations (0 µg/ml to 50 µg/ml) as indicated in FIG. 3.

Magainin 2 alone had little inhibitory effect on either strain of *S. aureus* (up to 50 µg ml$^{-1}$), but combination with lysostaphin resulted in significant synergistic inhibition (FIG. 3).

For example, visible growth was completely inhibited for 48 hours after exposure to 5 μg ml$^{-1}$ magainin 2 and 0.05 μg ml$^{-1}$ lysostaphin.

EXAMPLE 5

Figure 5A:
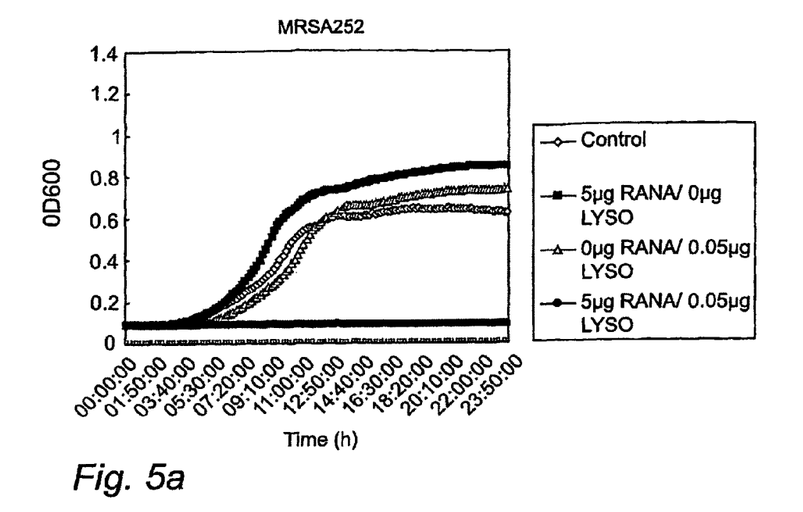
FIG. 5 shows graphs plotting OD600 for *Staphylococcus aureus* strains MRSA252 (a, c, e) and MSSA476 (b, d, f) measured over 24 hours with ranalexin, lysostaphin or a combination of both ranalexin and lysostaphin at different concentrations.
Figure 5B:
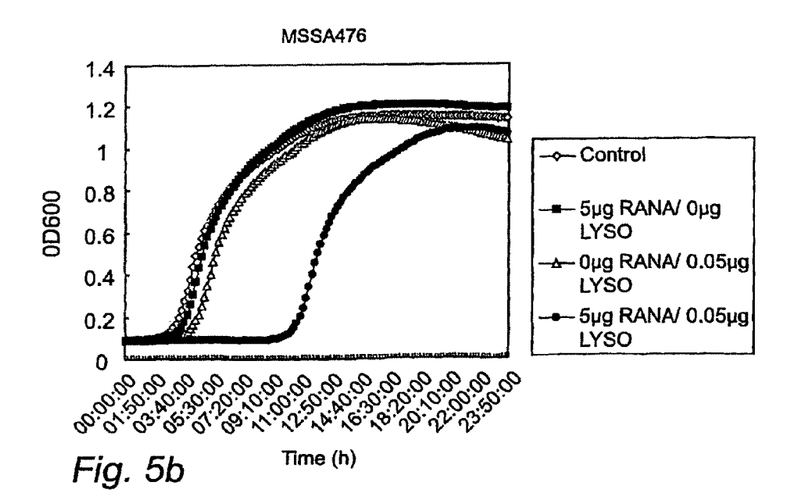
Figure 5C:
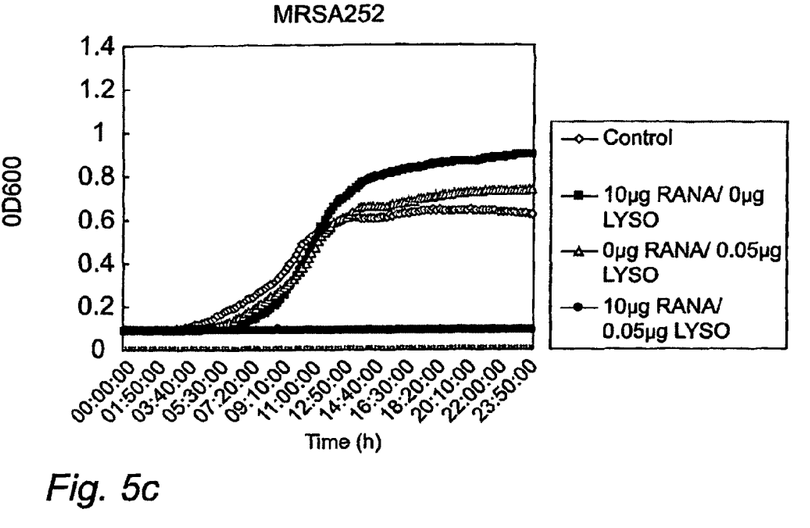
Figure 5D:
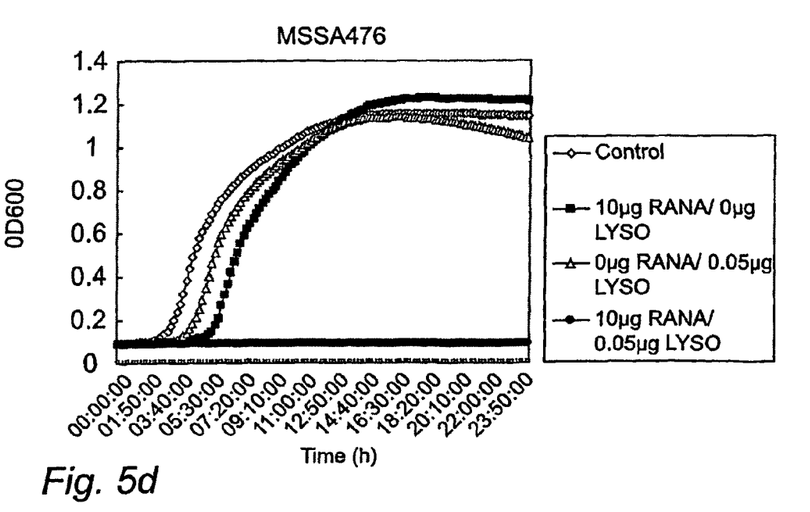
Figure 5E:
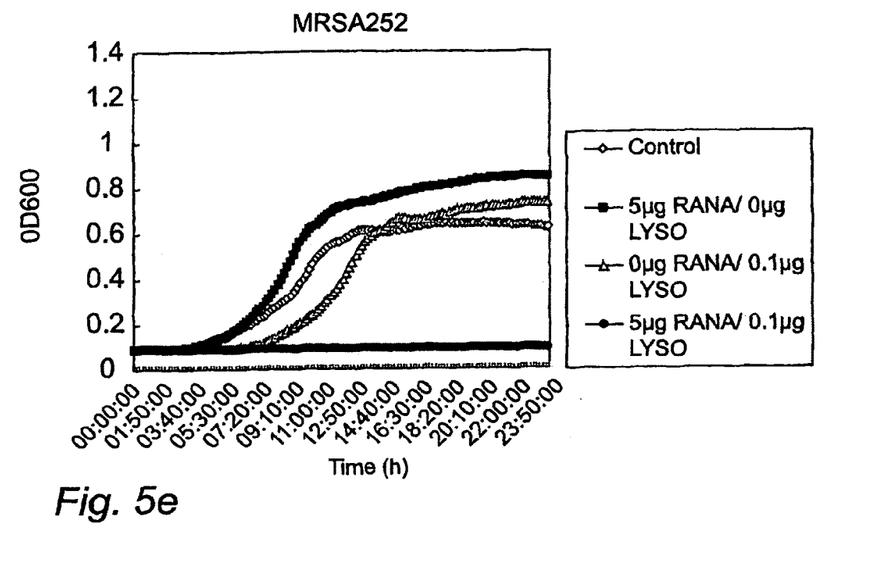
Figure 5F:
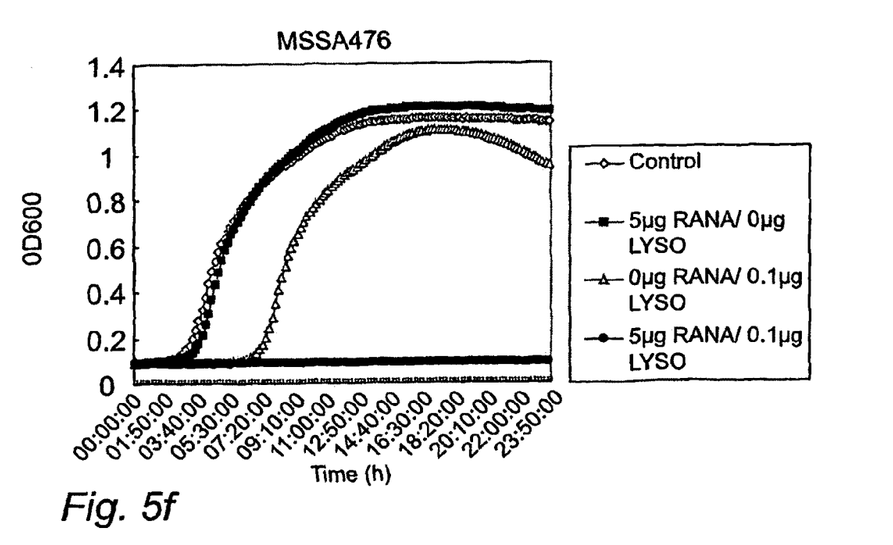

*Staphylococcus aureus* strains MSSA476 and MRSA252 were cultivated and placed into 96 well plates as described in Example 1. Plates were incubated at 37° C. with shaking for 24 hours in a PowerWave XS automated microplate spectrophotometer (Bio-tek Instruments Inc., Winooski, USA) with optical density (600 nm) readings taken every 11 min. Data was collected automatically using KC4 v.3.2 software (Biotek, Instruments Inc., Winooski, USA) and analysed in Microsoft Excel in TSB medium. The plates contained different concentrations of ranalexin, magainin2, dermaseptin s3(1-6) and lysostaphin, or combinations of lysostaphin and ranalexin, lysostaphin and magainin2, or lysostaphin and dermaseptin s3(1-6). Increase of optical density (OD) was measured at 600 nm and plotted against cultivation time (see FIGS. 5 and 6). The synergistic effect for a combination of ranalexin and lysostaphin is shown in FIG. 5. A combination of ranalexin and lysostaphin is compared to either ranalexin or lysostaphin alone for MRSA252 (a, c, e) and MSSA476 (b, d, f). The synergistic inhibitory effect on MRSA252 is obtained for the composition comprising 5 μg/ml ranalexin and 0.05 μg/ml lysostaphin (FIG. 5*a*). A synergistic effect for MSSA476 resulting in a delayed increase in OD600 can be observed for a ranalexin concentration of 5 μg/ml combined with 0.05 μg/ml lysostaphin (FIG. 5*b*), but total inhibition of growth over 24 hours is obtained at concentrations of 10 μg ranalexin/ml and 0.05 μg/ml lysostaphin (FIG. 5*d*) or 5 μg ranalexin/ml and 0.1 μg/ml lysostaphin (FIG. 5*f*).

Figure 6A:
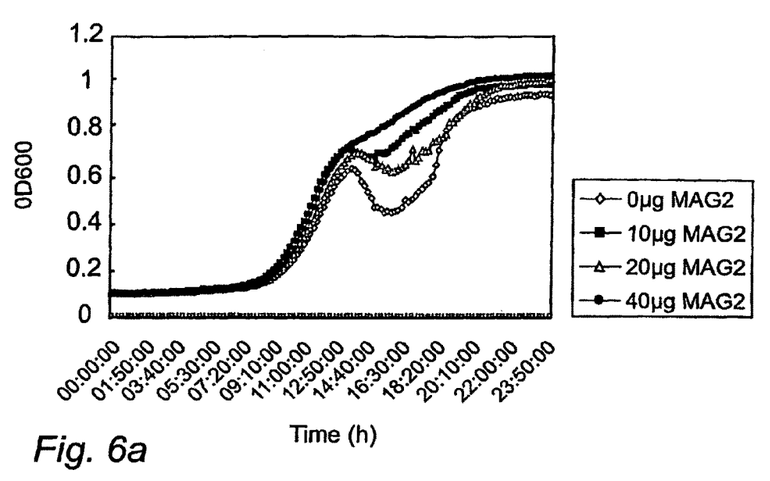
FIG. 6 shows graphs plotting OD600 of *Staphylococcus aureus* MRSA252 measured over 24 hours with only magainin2 (a), with only lysostaphin (b), and with a combination of magainin2 and lystostaphin (c). A similar experiment is shown plotting OD600 of *Staphylococcus aureus* MRSA252 measured over 24 hours with only dermaseptin s3(1-16) (d), with only lysostaphin (e) and with a combination of dermaseptin s3(1-16) and lysostaphin (f).
Figure 6B:
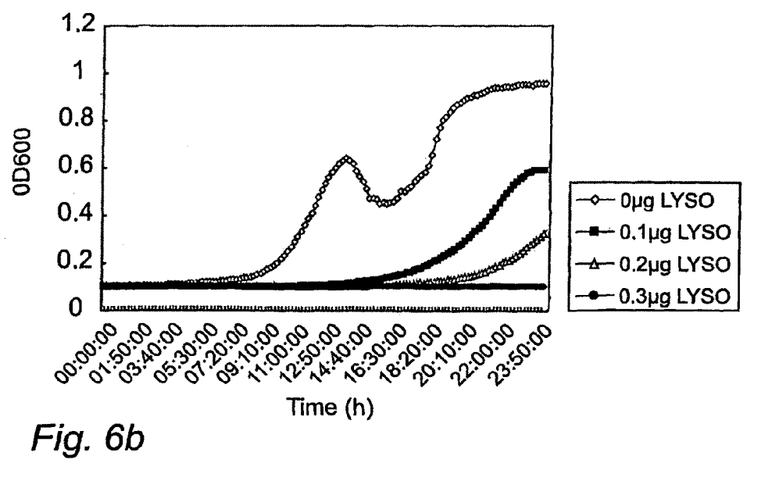
Figure 6C:
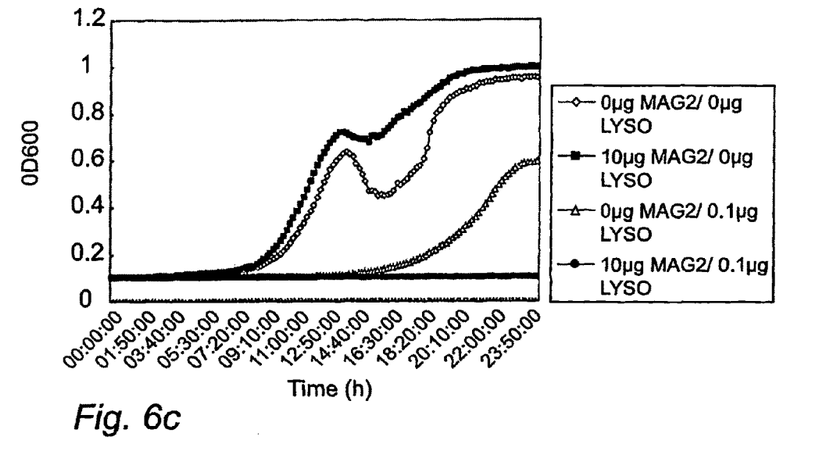
Figure 6D:
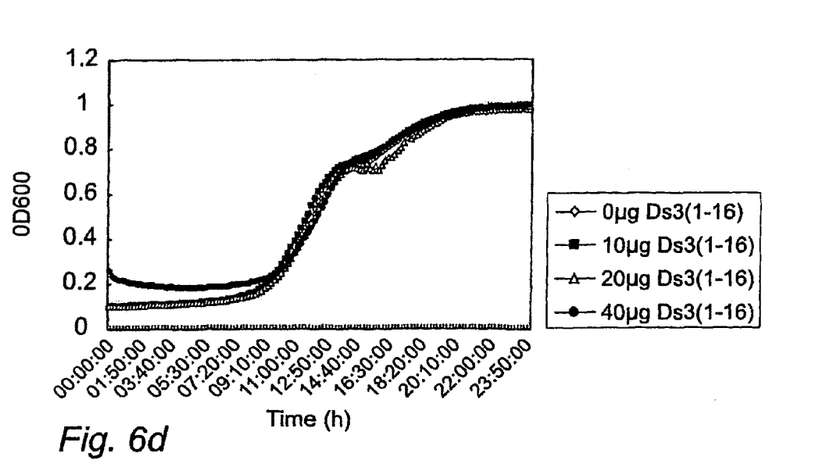
Figure 6E:
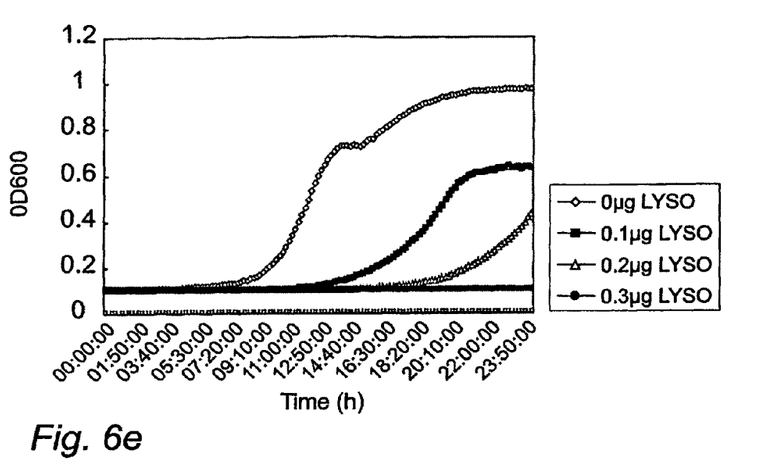
Figure 6F:
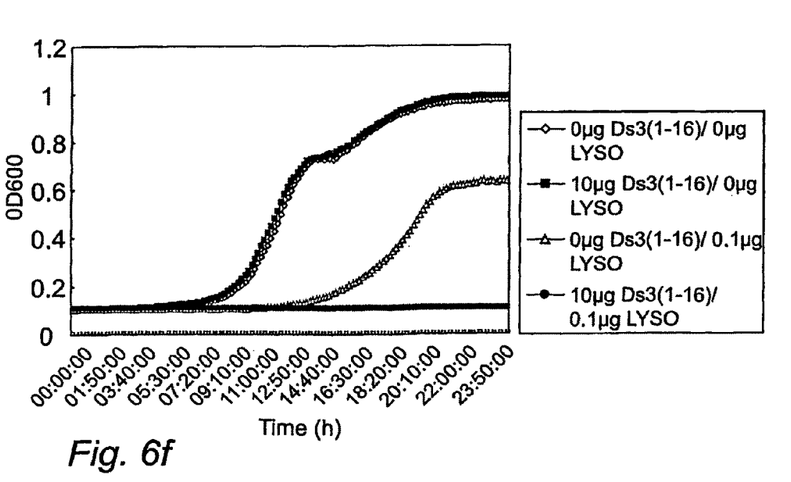

The synergistic effects for magainin2 and lysostaphin is shown in FIG. 6 (FIGS. 6*a, b, c*: magainin2 and lysostaphin, FIGS. 6*d, e, f*: dermaseptin s3(1-6) and lysostaphin). A combination of both compounds is compared to different concentrations of either magainin2 or lysostaphin. The synergistic inhibitory effect is obtained at a concentration of 10 μg/ml magainin2 and 0.1 μg/ml lysostaphin (FIG. 6*c*) and 10 μg/ml dermaseptin s3(1-16) and 0.1 μg/ml lysostaphin (FIG. 6*f*).

EXAMPLE 6

Figure 7:
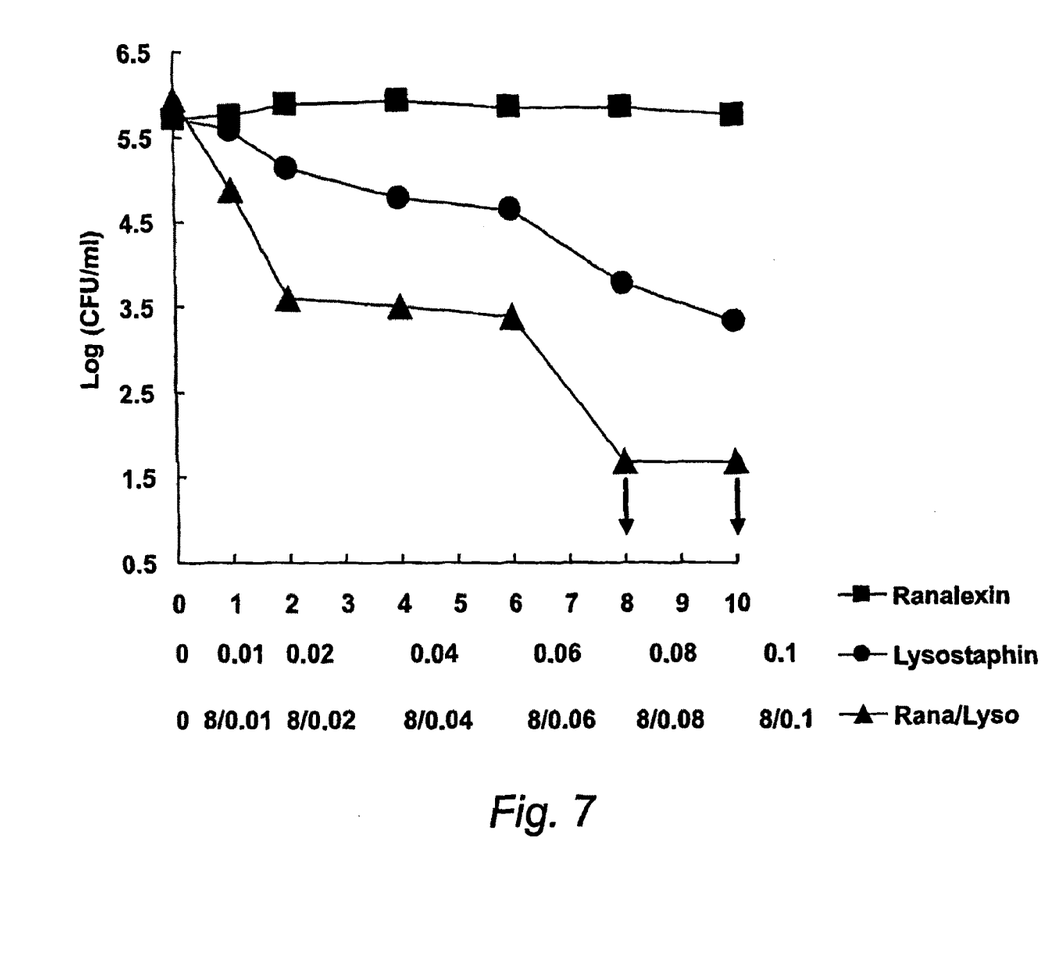
FIG. 7 is a graph showing an enhanced bactericidal effect against MRSA when lysostaphin is used in combination with ranalexin.

MRSA252 in TSB broth was exposed for 30 mins to either: increasing concentrations (0, 1, 2, 4, 6, 8 and 10 μg/ml) of ranalexin alone (filled squares); increasing concentrations (0.0, 0.01, 0.02, 0.04, 0.06, 0.08, 0.1 μg/ml) of lysostaphin alone (filled circles); or a combination of 8 μg/ml ranalexin with increasing concentrations (0.0, 0.01, 0.02, 0.04, 0.06, 0.08, 0.1 μg/ml) of lysostaphin. Total cell numbers, or survivors, after a 30 minute exposure to each of the above conditions were determined by serial dilution and plating on TSB agar. Survivors were determined after 24 hours incubation of the TSB plates at 37° C. and expressed as the log of colony forming units per ml of broth. The results are shown in FIG. 7. The arrows on FIG. 7 indicate that the numbers of survivors were less than the minimum detectable by this method.

As shown in FIG. 7, exposure to ranalexin concentrations up to 10 μg ml$^{-1}$ had no detectable effect on viability. Identical duration of exposure to increasing concentrations of lysostaphin, from 0.01 to 0.1 μg ml, resulted in a minor decrease in viable cell numbers. For example, 30 minutes exposure to 0.06 μg ml$^{-1}$ lysostaphin resulted in a 0.5-log reduction in numbers but exposure to 0.1 μg ml$^{-1}$ lysostaphin resulted in a 2-log (>99%) reduction. Notably, combination of 8 μg ml$^{-1}$ ranalexin with increasing concentrations of lysostaphin resulted in a dramatic reduction in viability after a 30 minutes exposure. For example, 8 μg ml$^{-1}$ ranalexin with 0.08 μg ml$^1$ lysostaphin resulted in greater than a 4 log reduction (beyond the limit of detection) in cell numbers (FIG. 7). Thus, the synergistic inhibition by ranalexin and lysostaphin results in an enhanced bactericidal effect.

EXAMPLE 7

Sterile Whatman paper disks were impregnated with ranalexin (0.5, 1, 2, 5, 10 or 20 μg), with lysostaphin (0.1, 0.2, 0.5, 1, 2 or 5 μg), a combination of 1 μg lysostaphin and ranalexin (0.5, 1, 2, 5, 10 or 20 μg), or a combination of 10 μg ranalexin and lysostaphin (0.2, 0.2, 0.5, 1, 2 or 5 μg). The paper disks were allowed to dry overnight and then stored at −20° C. until required.

Cultures of *Staphylococcus aureus* MRSA252 and *Staphylococcus aureus* MSSA476 were grown to mid-log phase (OD600 0.6-0.9) and diluted to 0.6 if necessary. 150 μl of the culture was then spread onto TSA (Tryptone Soya Agar; Oxoid, Basingstoke, UK) plates and allowed to dry. An impregnated paper disk prepared as described above was placed centrally on the agar plates. Plates were incubated for 20 hours at 37° C. before visual assessment of the zones of inhibition (see FIG. 8) which were visible as clear areas around the disks. From FIG. 8 it can be seen that some minimal inhibition occurred at a concentration of 20%μg ranalexin and at 5 μg lysostaphin, but not at lower concentrations of the agents when used alone.

Figure 8:
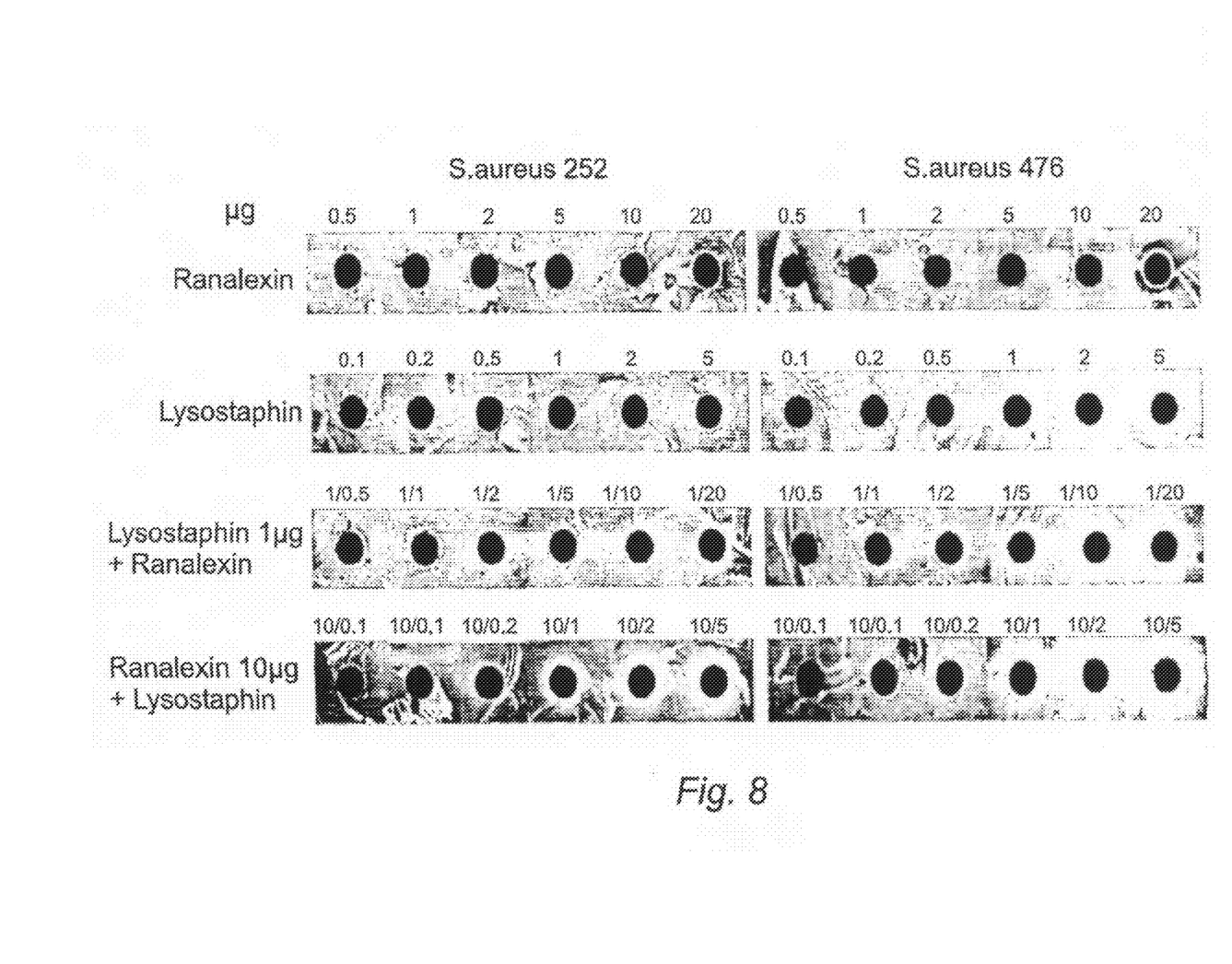
FIG. 8 shows growth inhibition of *Staphylococcus aureus* strains MRSA252 (left) and MSSA476 (right) on agar plates following introduction of paper disks impregnated with lysostaphin and/or ranalexin. Inhibition is illustrated by the zones of clearing around the paper disks.

However, exposure to disks impregnated with combinations of ranalexin and lysostaphin clearly revealed synergistic inhibition, with larger, more significant zones of inhibition (FIG. 8). For example, disks containing 1 μg ml$^{-1}$ lysostaphin but with increasing ranalexin, showed clear zones of inhibition with combinations above 10 μg ml$^{-1}$ ranalexin. Similarly, disks with a fixed concentration of ranalexin (10 μg ml$^{-1}$), but increasing lysostaphin (0.1-5 μg ml$^{-1}$), showed clear zones of inhibition with combinations above 1 μg ml$^{-1}$ lysostaphin. Compared to the zones of inhibition observed when testing conventional antibiotics, the zones observed with ranalexin and lysostaphin are smaller. With lysostaphin, this has been attributed to poor diffusion of the molecule through agar compared to conventional antibiotics (Kusuma & Kokai-Kum, 2005, Antimic Agents Chemother 49:3256-3263). Both lysostaphin and ranalexin are basic, charged proteins with molecular weights of 27 and 2.1 kDa respectively. The majority of conventional antibiotics are much smaller, with lower molecular weights, perhaps explaining the apparently small zones of inhibition observed with ranalexin and lysostaphin. Nevertheless, the results demonstrate that the synergistic combination effectively kills bacteria growing on a porous surface even after the compounds are added to a porous matrix and allowed to dry. Thus wounds infected with drug-resistant MRSA could be effectively treated with dressings or bandages impregnated with the two compounds. Other potential applications could include topical treatment of Staphylococcal skin infections, surface cleaner to remove MRSA and treatment of invasive medical devices, for example, catheters, sutures etc. to prevent infection with potentially life-threatening MRSA.

The invention claimed is:

1. A composition comprising lysostaphin and a cationic peptide which is ranalexin, dermaseptin S3 or a mixture thereof.

2. The composition as claimed in claim 1, wherein the composition inhibits propagation of a prokaryote.

3. The composition as claimed in claim 2, wherein the prokaryote is a Gram positive bacterium.

4. The composition as claimed in claim 3, wherein the Gram positive bacterium is *Staphylococcus* sp.

5. The composition as claimed in claim 4, wherein the bacterium is *Staphylococcus aureus*.

6. The composition as claimed in claim 5, wherein the bacterium is *Staphylococcus aureus* MRSA.

7. The composition as claimed in claim 1, wherein the cationic peptide and the lysostaphin are in the form of an aqueous solution or suspension.

8. The composition as claimed in claim 1, which comprises ranalexin and lysostaphin.

9. The composition as claimed in claim 8 comprising ranalexin at a concentration of 0.001 µg/ml to 100 µg/ml and lysostaphin at a concentration of 0.001 µg/ml to 100 µg/ml.

10. The composition as claimed in claim 9, comprising a concentration of 5 to 50 µg ranalexin/ml.

11. The composition as claimed in either one of claims 9 and 10, comprising a concentration of 0.15 to 1.05 µg lysostaphin/ml.

12. The composition as claimed in claim 1, which comprises dermaseptin and lysostaphin.

13. The composition as claimed in claim 12 wherein the dermaseptin is dermaseptin S3(1-16).

14. The composition as claimed in claim 12, comprising dermaseptin at a concentration of 0.001 µg/ml to 100 µg/ml and lysostaphin at a concentration of 0.001 µg/ml to 100 µg/ml.

15. The composition as claimed in claim 14, comprising a concentration of 5 to 50 µg dermaseptin/ml.

16. The composition as claimed in either one of claims 14 and 15, comprising a concentration of 0.05 to 0.5 µg lysostaphin/ml.

17. A wound dressing containing a composition as claimed in claim 1.

18. A solid porous matrix containing a composition as claimed in claim 1.

19. The matrix as claimed in claim 18 which is a bandage, wipe, swab, medical thread, surgical garment or a wound dressing.

20. A medical device or surgical instrument impregnated or coated with a composition as claimed in claim 1.

21. A method of combating a bacterial infection in a patient, said method comprising applying a composition as claimed in claim 1 to a body surface of said patient.

22. A method as claimed in claim 21, wherein said body surface is a wound.

23. The method as claimed in claim 21, for treating an existing bacterial infection in the patient.

24. The method as claimed in claim 21, for preventing a bacterial infection in the patient.

25. The method as claimed claim 21, wherein the composition is applied following an operation or surgery.

26. A method of combating a bacterial infection in a patient, said method comprising applying a wound dressing as claimed in claim 17 to a body surface of said patient.

27. A method of treating a surface of an object or a surface of a room to combat bacterial propagation thereon, said method comprising applying a composition as claimed in claim 1.

28. The method as claimed in claim 21 or 27, wherein said composition is applied as an aerosol spray.

29. A method of inhibiting propagation of a prokaryote, said method comprising applying a composition as claimed in claim 1 to a surface.

30. A method for inhibiting propagation of a prokaryotic organism by using a composition comprising a cationic peptide which is ranalexin, dermaseptin S3 or a mixture thereof and lysostaphin, wherein the prokaryotic organism has a cell wall comprising a phospholipid membrane comprising one or more acidic phospholipids and a mureinsacculus comprising at least two murein layers cross-linked via a peptide bridge comprising at least one peptide bond connecting at least two glycine residues, wherein said composition disintegrates said cell wall, and wherein said lysostaphin hydrolyses said peptide bond connecting the at least two glycine residues and wherein said cationic peptide interacts with said membrane.

\* \* \* \* \*